United States Patent [19]

Adkins, Jr. et al.

[11] Patent Number: 4,904,698

[45] Date of Patent: Feb. 27, 1990

[54] EYELID CLEANSING COMPOSITION

[75] Inventors: Nat G. Adkins, Jr., Richmond; Douglas S. Rooney, Grapevine, both of Tex.

[73] Assignee: OcuSoft Inc., Richmond, Tex.

[21] Appl. No.: 159,403

[22] Filed: Feb. 11, 1988

[51] Int. Cl.⁴ .................. A61K 31/14; A61K 31/74; A61K 31/79

[52] U.S. Cl. .................................. 514/642; 514/643; 514/839; 514/840

[58] Field of Search ................ 514/642, 643, 839, 840

[56] References Cited

U.S. PATENT DOCUMENTS 4,029,817  6/1977  Blanco et al. ................... 514/781
4,407,791  10/1983  Stark ................................ 514/642
4,420,484  12/1983  Gorman et al. ................. 514/642

*Primary Examiner*—John Kight
*Assistant Examiner*—Nathan M. Nutter
*Attorney, Agent, or Firm*—Price, LeBlanc, Becker & Shur Lowe

[57] ABSTRACT

A non-irritating liquid cleansing composition is described for cleansing eyelids. The composition includes an aqueous solution of Miranol MS-2 present in a concentration of 7-10%; PEG-15 tallow polyamine present in a concentration of 0.1-0.5%; sodium chloride present in a concentration of 0.6-0.9%; at least one microbiological preservative selected from the group consisting of Quaternium-15 and benzyl alcohol present in a concentration of 0.1-0.5%; and as an optional ingredient disodium EDTA present in a concentration of up to 0.1%. The composition is non-irritating to the eyes, has a pH of between 8.0 and 8.5, and a viscosity very similar to water.

5 Claims, No Drawings

EYELID CLEANSING COMPOSITION

BACKGROUND OF THE INVENTION

This invention relates to a non-irritating liquid composition useful in cleansing the eyelids.

Blepharitis is a common chronic inflammation of the eyelids characterized by a scaly crust on the lid margins The condition may be caused by a bacterial infection, or it may be allergic in origin or associated with seborrhea of the face and scalp. Treatment usually involves cleansing the eyelids on a regular basis.

Often associated with or secondary to blepharitis is a bacterial infection of the surface of the skin at the edge of the lid know as an external hordeolum or of the meibomian glands, either, commonly referred to as sties. Such conditions also are accompanied by pain, redness and tenderness of the lid margins. Although sties are often recurring, such conditions can be minimized by regular cleansing of the eyelid margins.

Glands in and around the lid margins secrete oil which in some individuals can build up in the eyelashes and on the lids. This build up of oil is usually accompanied with cellular debris, dust and the like. Obviously, if this build up is excessive, the likelihood of a bacterial infection will be increased.

Historically, blepharitis conditions have been treated by using "homemade" solutions of dilute baby shampoo. This required the patient to dilute the baby shampoo with tap water and then use the dilute solution with a cotton-tipped applicator pad or the like to cleanse the eyelids. An alternative composition whose primary component was aloe vera has been marketed. This composition however is not phase stable and therefore the patient must shake the solution before using. In both instances patient compliance with the procedure required for use was low. It is therefore necessary and desirable to have a lid cleansing solution which is usable without further dilution by the patient and which is phase stable and non-irritating.

SUMMARY OF THE INVENTION

It has been discovered that the combination of surfactants, amphoteric, non-ionic, an ionic, with preservatives, and emollients of this invention can provide a non-irritating and highly effective cleansing solution for eyelids.

The aqueous solution of this invention includes as a major ingredient a mixture of surfactants marketed by Miranol Chemical Company of Dayton, N.J., under the tradename MS-2. This mixture includes PEG-80 sorbitan laurate, sodium trideceth sulphate, PEG-150 distearate, cocamidopropylhydroxy sultaine, lauroamphocarboxy glycinate, and sodium laureth-13 carboxylate. The solution also includes sodium chloride, the emollient and surfactant PEG-15 tallow polyamine, a microbiological preservative which may be Quaternium-15, or benzyl alcohol, and optionally, a chelating agent such as disodium EDTA. Many of these compounds have been described for use in various cleansing solutions such as for example soft contact lens cleansing solutions. See U.S. Pat. Nos. 4,029,817 and 4,407,791. In addition, Quaternium-15 is well known as microbiological preservative and ingredient in skin cleansing compositions. See for example, U.S. Pat. No. 4,420,484. The overall combination of ingredients however has not been known in a non-irritating cleansing solution for eyelids.

The solution of this invention then is an aqueous nonirritating solution which has been found to be highly effective in lid cleansing either in blepharitis conditions, or on a regular basis to prevent recurrence of the build up of oil, debris and dust which can foster a bacterial infection.

Accordingly it is an object of this invention to provide a non-irritating lid cleansing solution which is phase stable, and freeze-thaw stable.

It is another object of this invention to provide a lid cleansing solution having a viscosity equivalent to that of water which is clear and non-irritating which may be applied on a regular basis by a patient to the eyelids to cleanse the same.

It is yet another object of this invention to provide a lid cleansing composition in aqueous solution utilizing surfactants and emollients which are both non-irritating and safe for topical application to the eyelids.

It is yet another object of this invention to provide an aqueous lid cleansing solution having as a major ingredient a mixture of surfactants identified as Miranol MS-2 together with a polyethylene glycol ester of tallow polyamine, a microbiological preservative and sodium chloride having a pH of 8.0-8.5 which is both phase stable and freeze-thaw stable for topical application to cleanse the eyelids.

These and other objects will become apparent with reference to the following description:

DETAILED DESCRIPTION OF THE INVENTION

The composition of this invention is an aqueous solution containing as a major ingredient about 7-10% by weight of the surfactant composition marketed under the tradename Miranol MS-2 by Miranol Chemical Company of Dayton, New Jersey. Also present is PEG-15 tallow polyamine in a concentration range of 0.1-0.5% by weight. This compound is a tertiary surfactant and emollient. Sodium chloride is also present in a concentration ranging from 0.6-0.9% whereby the pH of the composition will be in the range of 8.0-8.5.

In a preferred embodiment of this invention a microbiological preservative is included. The preservative preferred is Quaternium-15. This composition is N-(3-chloroallyl) hexamminium chloride, a quaternary ammonium salt marketed by Dow Chemical Company of Midland, Mich., under the tradename Dowacil 200. Quaternium-15 is present in a concentration range of 0.1-0.5%. In the alternative, benzyl alcohol may be substituted in a concentration also of 0.1-0.5%. Finally, a chelating agent such as disodium EDTA may be used in a concentration range of 0.01-0.1%.

As previously indicated, Miranol MS-2, the major ingredient in the composition of this invention is a combination of surfactants. As used herein the term Miranol MS-2 means a combination of the anionic surfactant sodium trideceth sulphate, a non-ionic thickener and emollient PEG-150 Distearate, and an amphoteric surfactant cocamidopropylhydroxy sultaine. In addition, there is included the polyoxyethylenesorbitan fatty acid ester PEG-80 sorbitan laurate, lauroamphocarboxy glycinate and sodium laureth-13 carboxylate.

EXAMPLE

The following table describes the preferred concentration of ingredients for the cleansing solution of the instant invention:

TABLE I

| Compound | Weight/Weight % |
| --- | --- |
| Miranol MS-2 | 8.13 |
| sodium chloride | 0.70 |
| PEG tallow polyamine | 0.16 |
| Quaternium-15 | 0.10 |
| deionized Water | Q.S to 100% |

The above composition was tested for irritation using albino rabbits of the New Zealand strain and the scoring method of J. H. Draize: Dermal Toxicity, "Appraisal of the Safety of Chemicals in Foods, Drugs and Cosmetics", *Association of Food and Drug Officials of the U.S.*, 1959, pages 59–51.

The test sample was instilled into the conjunctival sac of the right eye of each rabbit in accordance with the procedure outlined in general in the above article with the left eye serving as control. At each scoring interval the cornea, iris and palpebral conjunctivae were examined and graded for irritation and injury. Table II below describes the grades. In this scoring system special emphasis is placed upon irritation or damage to the cornea, while less emphasis is placed upon irritation to the iris or conjunctivae. A rating is obtained by scoring the maximum mean irritation score at 1, 24, 48 or 72 hours after installation of the sample. If the rate of dissipation of the injury did not meet the requirements defined for the descriptive rating appropriate for a particular numerical score, the descriptive rating is raised by one or more levels. Table III attached describes further the grading system.

TABLE II

Eye Irritation Test Descriptive Rating System

| Classificatin | Range | Definition |
| --- | --- | --- |
| Non-irritating | 0.0–0.5 | To maintain this rating, all scores at the 24-hour reading must be zero; otherwise, increase rating one level. |
| Practically Non-irritating | Greater than 0.5–2.5 | To maintain this rating, all scores at the 24-hour reading must be zero; otherwise, increase rating one level. |
| Minimally Irritating | Greater than 2.5–15.0 | To maintain this rating, all scores at the 72-hour reading must be zero; otherwise, increase rating one level. |
| Moderately Irritating | Greater than 15.0–25.0 | To maintain this rating, all scores at the 7-day reading must be zero; otherwise, increase rating one level. |
| Moderately Irritating | Greater than 25.0–50.0 | To maintain this ratng, scores at 7 days must be less than or equal to 10 for 60% or more of the animals. Also, mean 7-day scores must be less than or equal to 20. If 7-day mean score is less than or equal to 20 but less than 10, then no animal among those showing scores greater than 10 can exceed a score of 30 if rating is to be maintained; otherwise, increase rating one level. |
| Severely Irritating | Greater than 50.0–80.0 | To maintain this rating, scores 7 days must be less than or equal to 30 for 60% or more of the animals. Also, mean 7-day scores must be less than or equal to 40. If 7-day mean score is less than or equal to 40, but less than or equal to 30, then no animal among those showing scores greater than 30 can exceed a score of 60 if rating is to be maintained; |

TABLE II-continued

Eye Irritation Test Descriptive Rating System

| Classificatin | Range | Definition |
| --- | --- | --- |
| | | otherwise, increase rating by one level. |
| Extremely Irritating | Greater than 80.0–110.0 | |

TABLE III

Grades for Ocular Lesions

| CORNEA | |
| --- | --- |
| Opacity (D) - Degree of density | |
| Scattered or diffuse area, details of iris clearly visible | 1 |
| Easily discernible translucent areas, details of iris slightly obscured | 2 |
| Opalescent area, no details of iris visible, size of pupil barely discernible | 3 |
| Opaque, iris not visible | 4 |
| Area of Cornea Involved (A) | |
| One quarter (or less) but not zero | 1 |
| Greater than one quarter but less than one half | 2 |
| Greater than one half but less than three quarters | 3 |
| Greater than three quarters, up to whole area | 4 |
| Score equals D × A × 5    Total Maximum = 80 | |
| IRIS | |
| Values | |
| Folds above normal, congestion, swelling, circumcorneal injection (any or all of these or a combination of any thereof), iris still reacting to light (sluggish reaction is positive) | 1 |
| No reaction to light, hemorrhage, gross destruction (any or all of these) | 2 |
| Score equals Value × 5    Total Maximum = 10 | |
| CONJUNCTIVE | |
| Redness (R) - refers to palpebral conjunctiva only | |
| Vessels definitely injected above normal | 1 |
| More diffuse, deeper crimson red individual vessels not easily discernible | 2 |
| Diffuse beefy red | 3 |
| Chemosis (S) | |
| Any swelling above normal (includes nictating membrane) | 1 |
| Obvious swelling with partial eversion of the lids | 2 |
| Swelling with lid about half closed | 3 |
| Swelling with lids about half closed to completely closed | 4 |
| Discharge (D) | |
| Any amount different from normal (does not include small amounts observed in inner canthus of normal animals) | 1 |
| Discharge with moistening of lids and hairs adjacent to lids | 2 |
| Discharge with moistening of lids and hairs and considerable area around eye | 3 |
| Score equals (R + S + D) × 2    Total Maximum = 20 | |

The maximum total score is the sum of all scores obtained from the cornea, iris, and conjunctiva.

Table IV summarizes the results of these tests. As can be seen in Table IV, the rating is minimally irritating well within the requirements for a non-irritating lid scrub according to this invention.

TABLE IV

Rabbit Eye Irritation Results

FORM ADMINISTERED: 0.1 ml instilled into the eye
SPECIAL INSTRUCTIONS: No wash; 72 hour observation
MAXIMUM MEAN IRRITATION SCORE: 1.3/110.0
CLASSIFICATION: Minimally Irritating

| Tissue | Rabbit Number | 24 Hrs | 48 Hrs | 72 Hrs | 7 Days | 14 Days |
| --- | --- | --- | --- | --- | --- | --- |
| Cornea (D-A) | 1 | 0 | 0 | 0 | | |
| Iris | | 0 | 0 | 0 | — | — |
| Conjunctiva (R-S-D) | | 2 (1-0-0) | 0 | 0 | | |
| Total | | 2 | 0 | 0 | | |

TABLE IV-continued
Rabbit Eye Irritation Results

FORM ADMINISTERED: 0.1 ml instilled into the eye
SPECIAL INSTRUCTIONS: No wash; 72 hour observation
MAXIMUM MEAN IRRITATION SCORE: 1.3/110.0
CLASSIFICATION: Minimally Irritating

| Tissue | Rabbit Number | 24 Hrs | 48 Hrs | 72 Hrs | 7 Days | 14 Days |
|---|---|---|---|---|---|---|
| Cornea (D-A) | 2 | 0 | 0 | 0 | | |
| Iris | | 0 | 0 | 0 | — | — |
| Conjunctiva (R-S-D) | | 0 | 0 | 0 | | |
| Total | | 0 | 0 | 0 | | |
| Cornea (D-A) | 3 | 0 | 0 | 0 | | |
| Iris | | 0 | 0 | 0 | — | — |
| Conjunctiva (R-S-D) | | 2 (1-0-0) | 0 | 0 | | |
| Total | | 2 | 0 | 0 | | |
| Averages: | | | | | | |
| Cornea | | 0.0 | 0.0 | 0.0 | | |
| Iris | | 0.0 | 0.0 | 0.0 | — | — |
| Conjunctiva | | 1.3 | 0.0 | 0.0 | | |
| Total | | 1.3 | 0.0 | 0.0 | | |

CORNEA:
D = Density  Corneal Score = D × A × 5
A = Area     Maximum Score = 80
IRIS:
Value × 5    Maximum Score = 10
CONJUNCTIVA:
Redness = R  Conjunctival Score = (R + S + D) × 2
Swelling = S
Discharge = D  Maximum Score = 20

In summary, it has been discovered that a phase stable nonirritating aqueous composition can be provided according to the formula of this invention for patient use. The lid scrub composition of this invention can then be used by patients without dilution, further mixing or the like so that there will be a high patient acceptance of the composition. Use on a regular basis then will prevent the build up of oil, dust or the like which can harbor bacteria in the eyelids which in turn can cause irritation, blepharitis, sties, and the like. The composition of this invention uses as a major ingredient a combination of surfactants identified as Miranol MS-2 together with PEG-15 tallow polyamine, a microbiological preservative which may be Quaternium-15 or benzyl alcohol, and optionally a chelating agent, disodium EDTA. The aqueous solution of these compounds together with sodium chloride then has a pH of 8.0-8.5. The solution is clear, has a viscosity similar to water and a specific gravity of 0.987. Tests have shown that the material is phase stable and freeze-thaw stable.

This invention may be embodied in other specific forms without departing from the spirit or essential characteristics thereto. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A non-irritating, aqueous composition for cleansing eyelids comprising in approximate parts by weight: Miranol MS-2 surfactant mixture present in a concentration of 7-10%; PEG-15 tallow polyamine present in a concentration of 0.1-0.5%; sodium chloride present in a concentration of 0.6-0.9%, at least one microbiological preservative selected from the group consisting of Quaternium-15 and benzyl alcohol present in a concentration of 0.1 to 0.5%; and disodium EDTA present in a concentration of 0-0.1%.

2. The composition of claim 1 wherein said preservative is benzyl alcohol and disodium EDTA is present in a concentration of 0.01-0.1%.

3. The composition of claim 1 wherein said ingredients are present in the following approximate percentages by weight:

| | |
|---|---|
| Miranol MS-2 | 8.13 |
| PEG-15 tallow polyamine | 0.16 |
| sodium chloride | 0.70 |
| Quaternium-15 | 0.10 |

4. The composition of claim 1 wherein said ingredients are present in the following approximate percentages by weight:

| | |
|---|---|
| Miranol MS-2 | 8.13 |
| PEG-15 tallow polyamine | 0.16 |
| sodium chloride | 0.70 |
| benzyl alcohol | 0.20 |
| disodium EDTA | 0.05 |

5. The composition of claim 1 wherein the pH is 8.0-8.5.

* * * * *